United States Patent
Levitz et al.

(10) Patent No.: US 9,921,148 B2
(45) Date of Patent: Mar. 20, 2018

(54) POLARIZED LIGHT IMAGING APPARATUS AND METHODS THEREOF FOR SEPARATING LIGHT FROM A SURFACE OF A SAMPLE ITS DEEPER DIFFUSE LAYERS

(71) Applicant: MOBILEODT LTD, Tel Aviv (IL)

(72) Inventors: David Levitz, Tel Aviv (IL); Ariel Beery, Tel Aviv (IL)

(73) Assignee: MOBILEODT LTD., Tel Aviv (IL)

( * ) Notice: Subject to any disclaimer, the term of this patent is extended or adjusted under 35 U.S.C. 154(b) by 0 days.

(21) Appl. No.: 14/786,144

(22) PCT Filed: Apr. 20, 2014

(86) PCT No.: PCT/US2014/034736
§ 371 (c)(1),
(2) Date: Oct. 21, 2015

(87) PCT Pub. No.: WO2014/176136
PCT Pub. Date: Oct. 30, 2014

(65) Prior Publication Data
US 2016/0084751 A1 Mar. 24, 2016

Related U.S. Application Data

(60) Provisional application No. 61/814,306, filed on Apr. 21, 2013, provisional application No. 61/922,111, filed on Dec. 31, 2013.

(51) Int. Cl.
*G01J 4/00* (2006.01)
*G01N 21/21* (2006.01)
*G01N 21/956* (2006.01)

(52) U.S. Cl.
CPC .......... *G01N 21/21* (2013.01); *G01N 21/956* (2013.01); *G01N 2201/063* (2013.01)

(58) Field of Classification Search
CPC . G01N 21/21; G01N 21/956; G01N 2201/063
(Continued)

(56) References Cited

U.S. PATENT DOCUMENTS

2005/0128482 A1* 6/2005 Gibbs ................. G01N 21/21
356/364
2007/0038040 A1* 2/2007 Cense .................. A61B 3/1005
600/310
(Continued)

FOREIGN PATENT DOCUMENTS

EP 1870696 A1 12/2007
JP H10108857 A 4/1998
(Continued)

*Primary Examiner* — Hina F Ayub
(74) *Attorney, Agent, or Firm* — Roach Brown McCarthy & Gruber, P.C.; Kevin D. McCarthy

(57) ABSTRACT

A polarized light imaging apparatus is provided. In an embodiment, the apparatus comprises a light source for producing light beams; an illumination optic coupled to the light source for guiding the light beams towards the sample; a linear polarizer coupled to the illumination optic and configured to produce a linearly polarized light towards the sample respective of the light beams; a TIR birefringent polarizing prism (BPP) coupled to the sample to maximize a refraction difference between ordinary waves and extraordinary waves of light returning from the sample; and a detection optic unit coupled to the non-TIR BPP for guiding the light waves returning from the sample towards a single polarization sensitive sensor element (SE), the SE is configured to capture at least one frame of the sample respective of the light waves returning from the superficial single-scattering layer of the sample apart from the deeper diffuse layer.

11 Claims, 5 Drawing Sheets

(58) Field of Classification Search
USPC .......................................................... 356/365
See application file for complete search history.

(56) References Cited

U.S. PATENT DOCUMENTS

| | | | | |
|---|---|---|---|---|
| 2007/0159603 A1* | 7/2007 | Aruga | ................... | H04N 9/3105 |
| | | | | 353/20 |
| 2011/0273711 A1* | 11/2011 | Pagnoux | .............. | A61B 5/0059 |
| | | | | 356/367 |
| 2012/0069326 A1* | 3/2012 | Colonna de Lega | ................... | G01B 11/0675 |
| | | | | 356/73 |
| 2013/0136306 A1* | 5/2013 | Li | .......................... | G02B 27/28 |
| | | | | 382/103 |
| 2014/0118740 A1* | 5/2014 | Fontaine | ................. | G01M 11/30 |
| | | | | 356/364 |
| 2014/0303463 A1* | 10/2014 | Robinson | ........... | A61B 5/14552 |
| | | | | 600/316 |

FOREIGN PATENT DOCUMENTS

| | | | |
|---|---|---|---|
| JP | 2013033017 A | * | 2/2013 |
| WO | 2011132978 A2 | | 10/2011 |

\* cited by examiner

POLARIZED LIGHT IMAGING APPARATUS AND METHODS THEREOF FOR SEPARATING LIGHT FROM A SURFACE OF A SAMPLE ITS DEEPER DIFFUSE LAYERS

CROSS-REFERENCE TO RELATED APPLICATIONS

This patent application is a U.S. National Phase filing of commonly owned PCT Application No. PCT/US2014/034736, filed Apr. 20, 2014, which is based on and claims the benefit of the filing date of U.S. provisional patent application No. 61/814,306 filed on Apr. 21, 2013 and U.S. provisional patent application No. 61/922,111 filed on Dec. 31, 2013, all which are incorporated herein by reference for all that they contain in their entirety.

TECHNICAL FIELD

The invention relates generally to imaging platforms, and more specifically to a polarized light imaging apparatus for separation of light in imaging platforms.

BACKGROUND

Polarization imaging systems have typically been complex, expensive, and unsuitable for turbid media. Techniques of polarization difference imaging (PDI) systems are conventionally used for capturing a plurality of frames (e.g., images) of a sample. Such techniques are used to determine a spatial difference of the light intensity by comparing one frame of the sample to another.

When looking for a sample with a superficial structure in its single-scattering layer, the light returning from deeper structures can drown out light from a layer of interest. This drowning out occurs because most of the light returning from the sample (for example, 80% of the reflected light in skin) is diffuse. In addition, there is a specular reflection dependent on a refractive index of the sample and the angular extent of the illumination. Such specular reflection makes up roughly 15% of the reflected light. The layer of interest in the superficial single-scattering layer is thus about 4-5% of the reflected light. Removing this background signal allows for highlighting the layer of interest in the superficial structure. Eliminating the background signal is the key principle of the known PDI systems as a contrast enhancement mechanism. In the field of electrical engineering, an electrical circuit manipulating electricity in a similar way that PDI manipulates light is a common-mode rejection amplifier. Such an amplifier is typically utilized to reject noise or background signals (e.g., intensity drift of a light source).

The PDI systems typically include mechanically rotated optical polarizers or tunable liquid crystal polarizers. Techniques of PDI systems usually illuminate a sample with a polarized light and image the sample using at least one polarization sensitive sensor array. In such techniques the light is reflected from a sample surface (i.e., specular reflection) and the light backscattered from the sample surface maintains their wave properties, however, the diffuse light returning from the sample usually loses its polarization properties. This occurs because the light is split between two polarization channels: polarization parallel and polarization perpendicular.

A typical PDI system can be described mathematically as follows:

An incident light $(PAR)$=specular reflection+single-scattering $(SS)+\frac{1}{2}$*Diffuse; A cross-polarized light $(PER)=\frac{1}{2}$*Diffuse. The $PER$ is orthogonal to the $PAR$; and PDI=$PAR-PER$=specular reflection+SS.

Following is a detail description of the two conventional PDI systems discussed in the related art. A PDI system 100 shown with reference to FIG. 1 includes a sample 110 illuminated with a linearly polarized light. This is performed using a light source 120, an illumination optic 122 and a linear polarizer 124. The light (i.e., the specular reflection, the SS, and the diffuse) returning from the sample 110 is split between the two polarization channels by a polarizing beam splitter (PBS) 130. The split light is collected by a plurality of polarization sensitive sensor arrays (SAs) 140-1 and 140-2. Each sensitive SA 140-1, 140-2 is configured to capture at least one frame of the sample 110 respective of the two polarization channels showing in FIG. 1.

The linear polarizer 124 is located with respect to the PBS 130 in such a way that each of the SAs 140 is configured to capture either the PAR or the PER component. The illumination optic 122 is located between the light source 120 and the linear polarizer 124 in a way that enables a user to adjust the beams of light coming out from the light source 120 towards the sample 110. Similarly, a plurality of detection optic units (e.g., detection optic units 150-1 and 150-2) is located between the PBS 130 and each SA 140 to adjust the beams of light towards each SA 140.

Although the PDI system 100 is used by a variety of professionals, the system 100 holds some problems arising from its static nature. As an example, misalignments may occur between the SAs 140. Correcting these misalignments is inefficient in terms of complexity. In addition, a plurality of SAs 140 are required in order to capture the PAR and the PER by the system 100. This also holds disadvantages in terms of costs and complexity. Further, the system 100 is restricted by the polarization separating element (i.e., the PBS 130). Moreover, the system 100 described herein is unsuitable for the polarization of a turbid media.

Another conventional PDI system 200 is shown in FIG. 2. The system 200 illuminates a sample 110 of polarized light. The system 200 captures the PAR and PER components sequentially, as a function of time. That is, the light is polarized by a tunable polarizer 210 to illuminate the sample 110. The tunable polarizer 210 rotates the polarization by 90° between each frame captured by a SA 240, forming a square wave as a function of time. The light (being a combination of the specular reflection, the SS, and the diffuse) returning from the sample 110 is split between the two polarization channels by a liner polarizer 220.

The SA 240 is configured to capture multiple frames of the sample 110. The liner polarizer 220 is oriented either parallel or perpendicular to the polarization of the tunable polarizer 210 to yield PAR and PER images, respectively. The illumination optic 122 is located between the light source 120 and the tunable polarizer 210 to adjust the beams of light coming out from the light source 120 towards the tunable polarizer 210. Similarly, at least one detection optic 230 is located between the linear polarizer 220 and the SA 240 to adjust the beams of light toward the SA 240. In addition, the system 200 requires a control unit, such as a controller 250, to synchronize between the tunable polarizer 210 and the frame capturing function.

Although the system 200 is used by a variety of professionals, the system 200 holds some problems arising from its non-static nature. As an example, interruptions in the rotation of the polarization can occur, thereby causing the system 200 to be inefficient and unreliable. Thus, the rotation of the polarization is inefficient in terms of complexity. In addition, the system is restricted by the polarization separating element (i.e., the linear polarizer 220). Moreover, the system 200 is expensive and unsuitable for turbid media.

The two conventional PDI systems rely on the separation of the various polarizations either in space, onto separate SAs 140, or in time, on separate frames of the same SA 240, using a polarization separating element. Images or sub-images are combined to make an output image of the PAR and PER.

It would be therefore advantageous to provide a solution that overcomes the deficiencies of conventional PDI systems and techniques for separating the light returning from a superficial layer or a surface of a sample and the light returning from one or more deeper layers.

SUMMARY

Certain embodiments disclosed herein include a polarized light imaging apparatus for separating light from a superficial single-scattering layer of a sample and its deeper diffuse layer as a function of space. The apparatus comprises a light source for producing light beams; an illumination optic coupled to the light source for guiding the light beams towards the sample; a linear polarizer coupled to the illumination optic, wherein the linear polarizer is configured to produce a linearly polarized light towards the sample respective of the light beams; a non-total internal reflection (TIR) birefringent polarizing prism (BPP) communicatively coupled to the sample to maximize a refraction difference between ordinary waves and extraordinary waves of light returning from the sample; and a detection optic unit coupled to the non-TIR BPP for guiding the light waves returning from the sample towards a single polarization sensitive sensor element (SE), wherein the SE is configured to capture at least one frame of the sample respective of the light waves returning from the superficial single-scattering layer of the sample apart from the deeper diffuse layer.

Certain embodiments disclosed herein also include a method for separating light from a superficial single-scattering layer of a sample and its deeper diffuse layer as a function of space. The method comprises enabling a light source to generate light beams, wherein the light beams are guided towards the sample; producing a linearly polarized light respective of the light beams; enabling a non-total internal reflection (TIR) birefringent polarizing prism (BPP) to maximize a refraction difference between ordinary waves and extraordinary waves of light returning from the sample; capturing a frame of the sample respective of light waves returning from the sample containing an incident light (PAR) and a cross-polarized light (PER), wherein the returning light waves are adjusted by a detection optic unit; and producing an output image showing the PAR component and the PER component respective of the captured frame.

Certain embodiments disclosed herein further include a polarized light imaging apparatus for separating light from a superficial single-scattering layer of a sample and its deeper diffuse layer as a function of time. The system comprises a controller; a first light source for producing light beams with at least a first polarization feature under the control of the controller respective of a first predetermined time interval; a second light source for producing light beams with at least a second polarization feature under the control of the controller respective of a second predetermined time interval; a first illumination optic coupled to the at least a first light source, wherein the first illumination optic guides the light beams produced by the first light source towards the sample; a second illumination optic coupled to the at least a second light source, wherein the second illumination optic guides the light beams produced by the second light source towards the sample; a first linear polarizer coupled to the first illumination optic, wherein the first linear polarizer is configured to produce a first linearly polarized light toward the sample respective of the light beams with at least a first polarization feature; a second linear polarizer coupled to the second illumination optic, wherein the second linear polarizer is configured to produce a second linearly polarized light toward the sample respective of the light beams with at least a second polarization feature; a third linear polarizer coupled to a detection optic unit, wherein the third linear polarizer is configured to produce a third linearly polarized light toward the sample respective of the light returning from the sample; and a single polarization sensitive sensor element (SE) for capturing a plurality of frames of the sample respective of the detection optic unit.

According to an embodiment, each of the plurality of frames is captured respective of at least a first unique polarization in a first predetermined time interval and the at least a second unique polarization in a second predetermined time interval. According to another embodiment, the polarization states of the first illumination optics and the second illumination optics is distinguished by sequencing. This may be done by interspersing illumination markers by a plurality of illumination optics separate and distinct from the two polarized optics described. This may include distinct wavelengths or an absence of illumination directed into the sample.

Certain embodiments disclosed herein further include a method for separating light from a superficial single-scattering layer of a sample and its deeper diffuse layer as a function of time. The method comprises enabling a first light source to generate a light beam with a first polarization features respective of a first predetermined time interval, wherein the light beams are guided by a first illumination optic towards the sample; producing a first linearly polarized light by at least a first linear polarizer respective of the guided light beams with at least a first polarization features; enabling a second light source to generate a light beams with a second polarization features respective of a second predetermined time interval, wherein the light beams are guided by a second illumination optic towards the sample; producing a second linearly polarized light by a second linear polarizer respective of the guided light beams with a second polarization features; capturing by a sensitive sensor element (SE) a first frame of the sample respective of light returning from the sample responsive of the a first unique polarization, wherein the returning light is proceeded by a third linear polarizer and adjusted by a detection optic; capturing by the SE a second frame of the sample respective of the light returning from the sample responsive of the second unique polarization, wherein the returning light is illuminated by the third linear polarizer and adjusted by the detection optic; returning the first frame and the second frame to produce an output image representing the differences between the first unique polarization and the second unique polarization.

According to an embodiment, the polarization states of the first illumination optic and the second illumination optic may be distinguish by sequencing. This may be done by interspersing illumination markers by a plurality of illumination optics separate and distinct from the two polarized optics described. This may include distinct wavelengths or an absence of illumination directed into the sample.

The various embodiment disclosed herein may be utilized for contrast enhancement and layer separation. The separation is performed by the processing unit in the outcome image of a superficial single-scattering layer of a sample from its deeper diffuse layer. In order to improve contrast between the superficial single-scattering layer and the deeper diffuse layer of the sample, excess light functioning as a background that dwarfs the signal is removed.

BRIEF DESCRIPTION OF THE DRAWINGS

The subject matter disclosed herein is particularly pointed out and distinctly claimed in the claims at the conclusion of the specification. The foregoing and other objects, features, and advantages of the disclosed embodiments will be apparent from the following detailed description taken in conjunction with the accompanying drawings.

DETAILED DESCRIPTION

Figure 1:
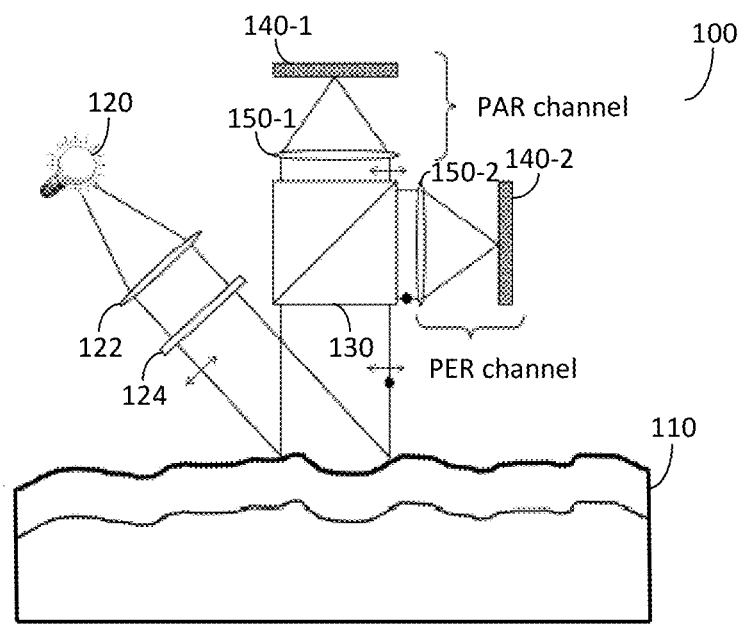
FIG. 1 is a schematic block diagram of a static polarization difference imaging (PDI) system operative.

It is important to note that the embodiments disclosed herein are only examples of the many advantageous uses of the innovative teachings herein. In general, statements made in the specification of the present application do not necessarily limit any of the various claimed inventions. Moreover, some statements may apply to some inventive features but not to others. In general, unless otherwise indicated, singular elements may be in plural and vice versa with no loss of generality. In the drawings, like numerals refer to like parts through several views.

Certain exemplary embodiments disclosed herein provide an apparatus and method for analyzing optical properties of a sample in its deep diffuse layer while separating the superficial layer for the purpose of identifying the state of the sample. As an example and without limitation, a turbid media such as a tissue sample of a human is analyzed to identify development of a tumor. According to an embodiment, a frame of a sample is captured by the disclosed apparatus containing a light source, one or more illumination optics, a linear polarizer, a birefringent polarizing prism (BPP), a detection optic, one or more aperture stops, and a single polarization sensitive sensor element (SE) configured to capture the frame of the sample as a function of space.

The captured frame is analyzed by a processing unit communicatively connected to the SE to produce an image showing the optical properties of the sample. Such an image is then displayed on a display. It should be noted that the SE is configured to capture both the incident light (PAR) component and the cross-polarized light (PER) component simultaneously in one frame.

According to another embodiment, a plurality of frames of a sample are captured by the disclosed apparatus containing a plurality of light sources, a plurality of illumination optics, a plurality of linear polarizers, one or more detection optics and a SE configured to capture the frames of the sample. It should be noted that each frame is typically captured in a different point in time and may be configured with different polarization properties. The frames are analyzed by a processing unit communicatively connected to the SE to produce an output image showing the differences between the polarization properties. The output image is then displayed on a display.

Figure 3:
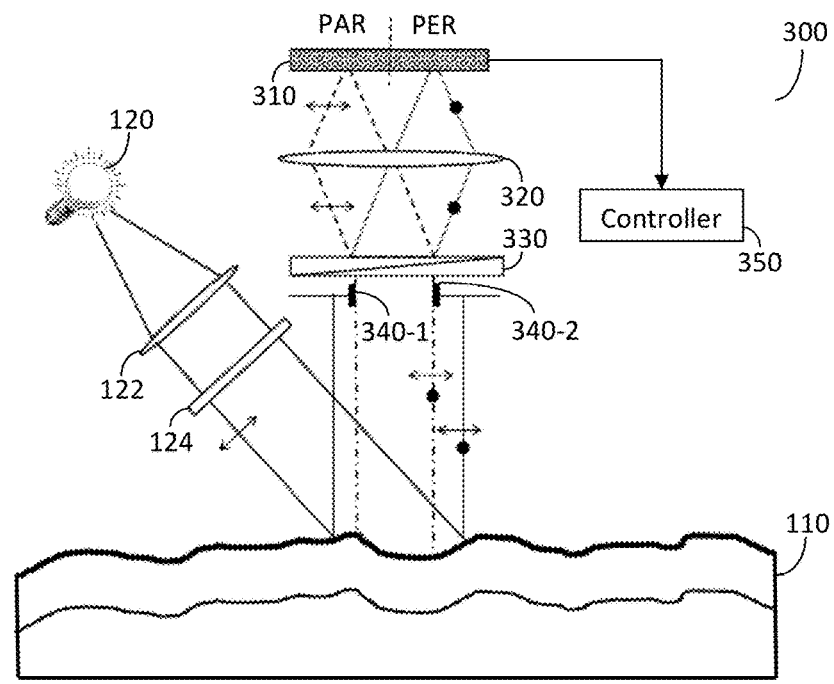
FIG. 3 is a schematic block diagram of a polarized light imaging apparatus for capturing at least one frame of a sample as a function of space according to an embodiment.

FIG. 3 shows an exemplary and non-limiting schematic diagram of a polarized light imaging apparatus 300 according to one embodiment. The apparatus is utilized to capture at least one frame of a sample such as, for example, a sample 110, as a function of space according to an embodiment. The sample 110 includes a surface, a superficial scattering layer, and a deep diffuse layer.

Figure 2:
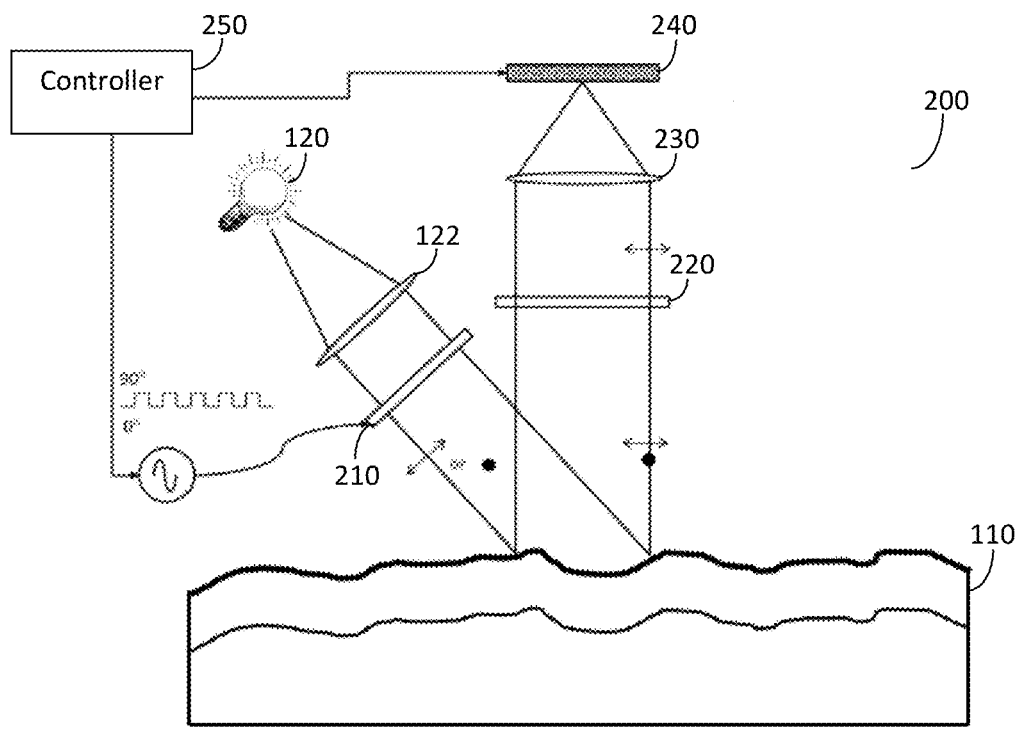
FIG. 2 is a schematic block diagram of a non-static PDI system operative.

The apparatus 300 includes a light source 120, an illumination optic, such as, illumination optic 122, a linear polarizer, such as a linear polarizer 124, a single polarization sensitive element (SE) 310, at least one detection optic unit 320, a non-total internal reflection (TIR) birefringent polarizing prism (BPP) 330, one or more aperture stops 340, for example, aperture stop 340-1 and aperture stop 340-2, and a controller 350. The structure and the functions of the controller 350 are described in detail herein below with respect to FIG. 5. The light source 120, the illumination optic 122, and the linear polarizer 124 are discussed above with respect to FIGS. 1 and 2.

According to an embodiment, the light source 120 is configured to produce square waves of light that proceed toward the sample 110. According to another embodiment, the light source 120 may be a tunable light source in which the wavelength is swept in time. The illumination optic 122 is coupled to the light source 120, and it is used to lead beams of light transmitted from the light source 120 towards the sample 110.

The sample 110 is illuminated by the linear polarizer 124 configured to produce a linearly polarized light respective of the generated light beams. The light waves returning from the sample 110, such as, a specular reflection, a single-scattering (SS), and diffuse are guided by the detection optic unit 320 towards the SE 310.

In an embodiment, the SE 310 is configured to capture at least one frame of the sample 110 respective of the returning light and the sensitive polarization. It should be noted that each frame captured by the SE 310 is taken in accordance with an incident light (PAR) and a cross-polarized light (PER). According to an embodiment, the PAR and PER may be captured by the SE 310 at the same magnification and orientation as shown below with reference to FIG. 6.

Capturing of the PAR and PER on the single SE 310 is enabled respective of the non-TIR BPP 330. Such non-TIR BPP 330 may be, but is not limited to, a Wollaston prism, a Nomarski prism, a Rochon prism, a Senarmont prism, and other optical systems that may be designed to function similar to the like. The non-TIR BPP 330 contains cemented birefringent crystals cut at its angles. Such a structure maximizes a refraction difference between ordinary and extraordinary waves, and allows the PAR and PER component to be captured on a single SE 310 at the same time.

In an embodiment, the aperture stops 340-1 and 340-2 are coupled to the non-TIR BPP 330. Each aperture stop 340-1, 340-2 is configured with a variable diameter that enables regulation of the amount of waves transmitted through the respective aperture stop 340-1 or 340-2 toward the non-TIR BPP 330. Such an amount of waves may be determined respective of a focus required in the produced polarization image.

The apparatus 300 described herein is utilized to identify optical properties such as a spatially diffuse reflectance of the sample 110. The sample 110 may include a turbid media. The optical properties are identified with respect to the sample 110 deep diffuse layer, while separating the superficial layer. In order to identify the optical properties of the sample 110, each frame captured by the SE 310 is analyzed to produce an output image under the control of a controller, such as the controller 350 as further described below with respect to FIG. 5.

As a non-limiting example, the apparatus 300 described herein may be utilized in medical imaging. In one embodiment, the apparatus 300 can be utilized for the analysis of an epithelial tissue when optical properties identification is required, typically in order to determine whether cancer developed on the superficial layer, for example, in a case of cervical cancer. In order to identify a malignant growth or tumor related to cervical cancer, the difference between the PAR and the PER components is determined. This is performed to separate the diffuse component from the specular reflection and the single-scattered (SS) components.

Figure 4:
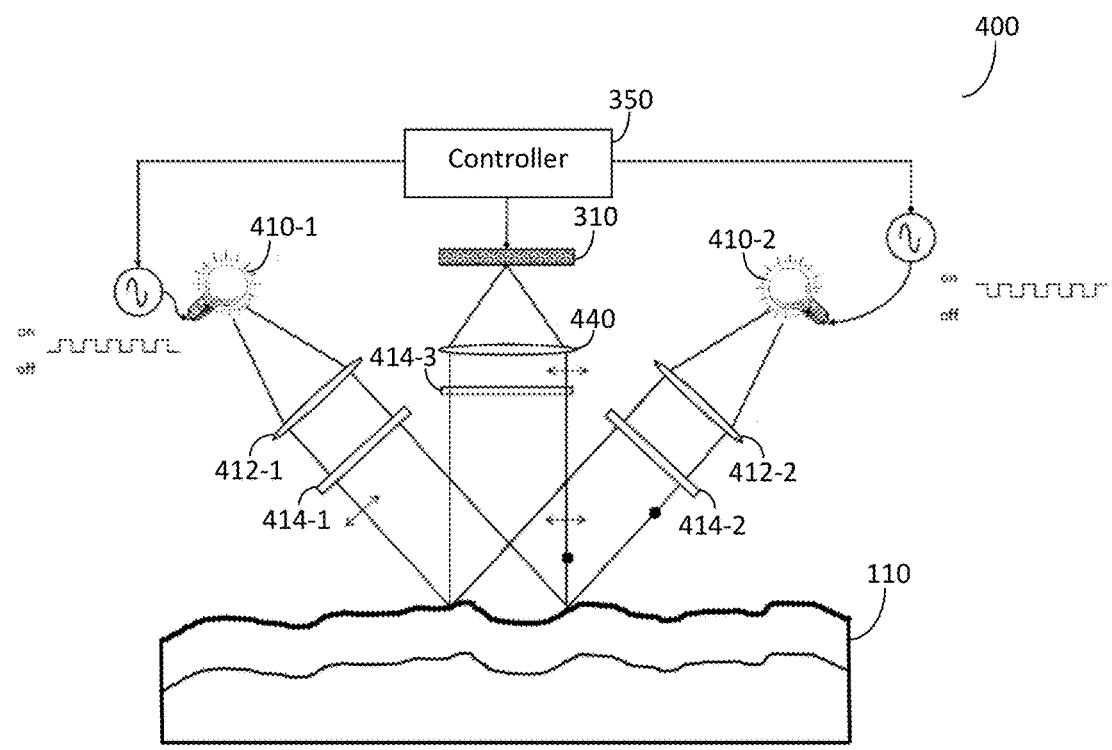
FIG. 4 is a schematic block diagram of a polarized light imaging apparatus for capturing a plurality of frames of a sample as a function of time according to an embodiment.

FIG. 4 depicts an exemplary and non-limiting schematic block diagram of a polarized light imaging apparatus 400 utilized to capture different illumination configurations according to an embodiment. The apparatus 400 includes a plurality of light sources such as, for example, light source 410-1 and light source 410-2, a plurality of illumination optics (e.g., illumination optic 412-1 and illumination optic 412-2), a plurality of linear polarizers (e.g., linear polarizer 414-1, linear polarizer 414-2, and linear polarizer 414-3), a detection optic unit 440, and a SE 310. The apparatus 400 also includes a controller 350; the structure and the functions of the controller 350 are described in detail herein below with respect to FIG. 5.

Each light source 410 is equipped with a polarization separating mechanism. Therefore, each light source 410 is configured to produce light beams with a unique polarization towards a sample 110 under the control of the controller 350. As an example, each light source 410-1, 410-2 may be a LED, a polarizer, a plastic light pipe, etc.

Each light source 410-1, 401-2 is coupled to an illumination optic 412-1, 412-2 respectively. Each illumination optic 412 is used to guide the light beams transmitted from each light source 410 toward the sample 110. In addition, each illumination optic 412 is coupled to one of the plurality of linear polarizers, e.g., 414-1 or 414-2. Each of the linear polarizers 414-1 and 414-2 is configured to produce a linearly polarized light respective of the light beams transmitted from the respective light source 410 and guided by the illumination optic 412.

In an embodiment, the apparatus includes additional linear polarizer 414-3 coupled to the detection optic unit 440. Such linear polarizer 414-3 is configured to transmit light that is linearly polarized (e.g., within orientation of 180°) or, alternatively, circularly polarized light to the detection optic unit 440. Then the detection optic unit 440 guides the polarized light towards the SE 310.

The SE 310 is configured to capture a plurality of frames of the sample 110. Each of the frames is captured respective of a unique polarization of the light sources 410 either by coordinating the illumination according to a predetermined time interval or by distinguishing between polarization states based on predetermined markers interspersed between the unique polarization states. The captured frames are analyzed under the control of the controller 350 to produce an output image that represents the difference between the various polarizations. This is further discussed herein below with respect to FIG. 5.

According to an embodiment, the apparatus 400 may also include a plurality of waveguides, such as a light pipe (not shown), coupled to each light source 410. Each waveguide is used to guide the light beams (or waves) generated by each light source 410-1 or 410-2.

As a non-limiting example, the apparatus 400 described herein is utilized for improving layer visualization through a layer separation. In addition, the apparatus 400 can be used in fingerprint identification, camouflage unmasking, and similar applications where the foreground and background of a sample can be distinguished. This is enabled because the polarization properties of light are better maintained for some polarizations more than others. As an example, the light that propagates through the sample 110 containing turbid media is diffused.

Figure 5:
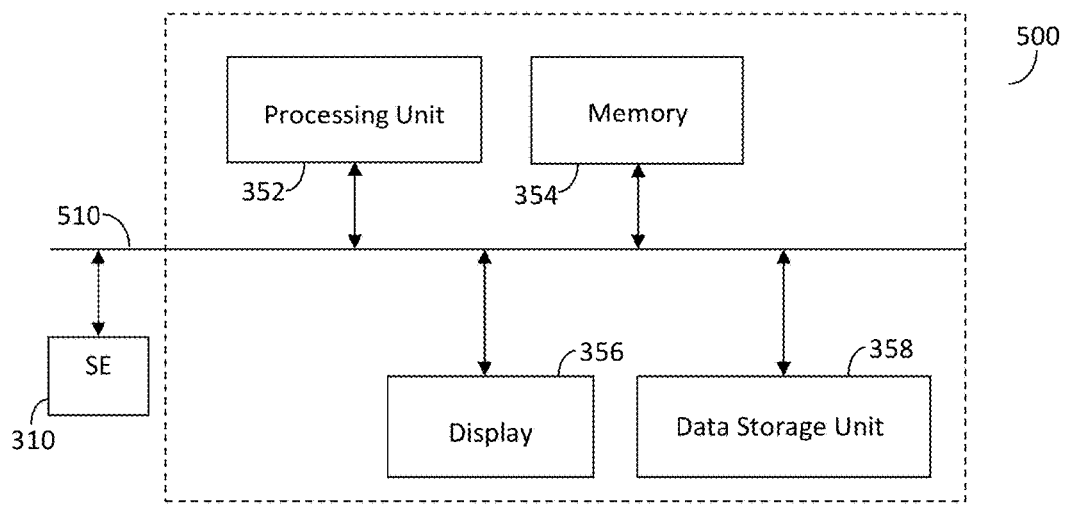
FIG. 5 is a schematic block diagram of a controller utilized to produce an output image according to an embodiment.

FIG. 5 depicts an exemplary and non-limiting schematic block diagram 500 of a controller 350 implemented according to one embodiment. As noted above, the controller 350 is communicatively connected to the SE 310. The controller 350 comprises a processing unit 352 that is communicatively connected to a memory unit such as memory 354. The memory 354 may contain, among other things, a plurality of instructions that, when executed by the processing unit 352, results in production of an output image from one or more frames captured by the SE 310 respective of the various polarizations. Such an image may be graphically represented on a display 356 communicatively connected to the processing unit 352.

The controller 350 also includes a data storage unit 358. The data storage unit 358 may be a part of the memory unit 354, or may be connected thereto as an external component. The data storage unit 358 typically holds data regarding the captured frames, the analysis performed, the produced polarized images and other relevant data used by the processing unit 352.

According to an embodiment, the various components shown herein are communicatively connected to the SE 310 via a communication bus 510. Such a connection may be a mere local bus, but, without limitation, the connection may be a data communication network of any sort and combination.

The production of an output image includes analyzing by the processing unit 352 at least one frame captured by the SE 310. The analysis is performed based on the instruction stored in the memory 354 respective of the type of the apparatus 300 or 400.

According to an embodiment, the processing unit 352 is configured to produce an image showing the PAR and the PER component when the SE 310 captures a frame of the sample 110 as a function of space. According to this embodiment, a single light source, such as light source 120, generates light beams, which are illuminated by a single linear polarizer such as linear polarizer 124, to be captured by the SE 310 as further discussed herein below with respect to FIG. 8.

According to another embodiment, the processing unit 352 is configured to produce an output image showing the differences between various polarizations when a plurality of frames are captured as a function of time. According to this embodiment, a plurality of light sources such as light sources 410 produces light beams with a unique polarization with either a predetermined time interval or a predetermined sequence. Such light beams are illuminated by a plurality of linear polarizers such as linear polarizers 414, and are captured by the SE 310 as a function of time. In such a case, the plurality of frames is analyzed to produce one or more polarization images respective of a required layer separation. This process is discussed herein below with respect to FIG. 9.

According to various embodiments the controller 350 or processing tasks performed by the controller 350 may be implemented by a handheld or worn computing device such as, but not limited to, a smart phone, a tablet computer, a notepad computer, smart eyeglasses of the variety of Google Glass, and the like. In an embodiment, the SE 310 is coupled to a camera of such computing device and the light source 120 is a flash light of the camera. In such an embodiment, a memory unit of the computing device would include instructions that, when executed by the processor of the device, would result in an output image generated from one or more frames captured by the SE 310 respective of the various polarizations. The produced image can be displayed on a display of the handled computing device.

Figure 6:
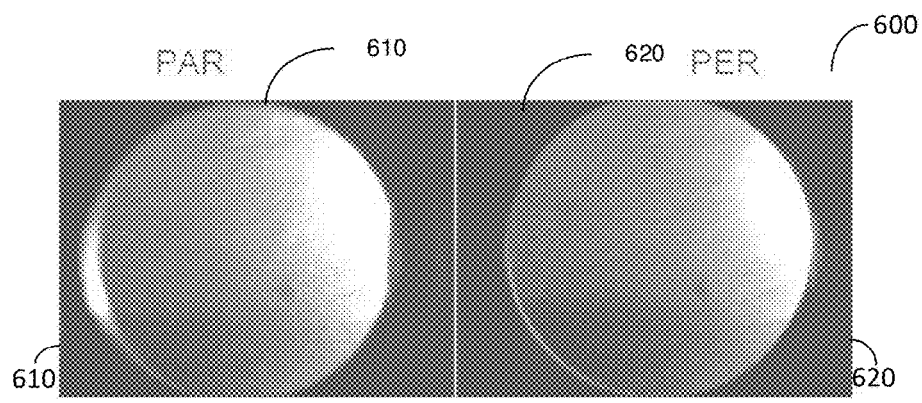
FIG. 6 is an image reconstruction of a sample showing an incident light (PAR) component and a cross-polarized light (PER) produced simultaneously according to an embodiment.

FIG. 6 depicts an exemplary and non-limiting image 600 illustrating reconstruction of a sample showing the PAR and the PER components achieved using the embodiments disclosed herein. The image 600 is produced by the processing unit 352 respective of a frame of the sample 110 captured by the SE 310 as a function of space. The image 600 shows a skin of a human forearm containing the PAR component 610 and PER component 620 side by side.

Figure 7:
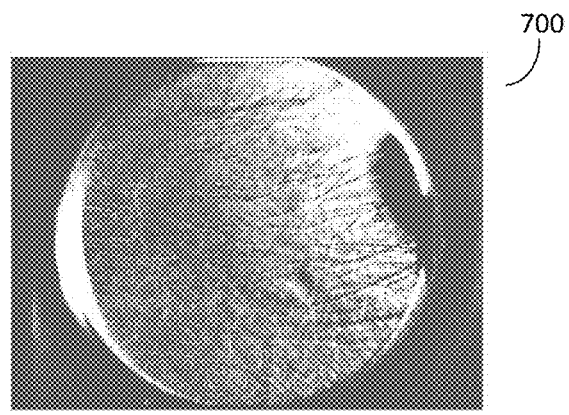
FIG. 7 is an image reconstruction of a sample showing the difference between the PAR component and the PER component.

FIG. 7 depicts an exemplary and non-limiting image 700 of the reconstruction of a sample showing the difference between the PAR and the PER produced according to the disclosed embodiments. The exemplary image 700 may be produced by the processing unit 352 respective of a frame of the sample 110 captured by the SE 310 as a function of space. The image 700 may be produced respective of instructions stored in the memory 354 to show a linear combination of the PAR and the PER component with respect of FIG. 6.

Figure 8:
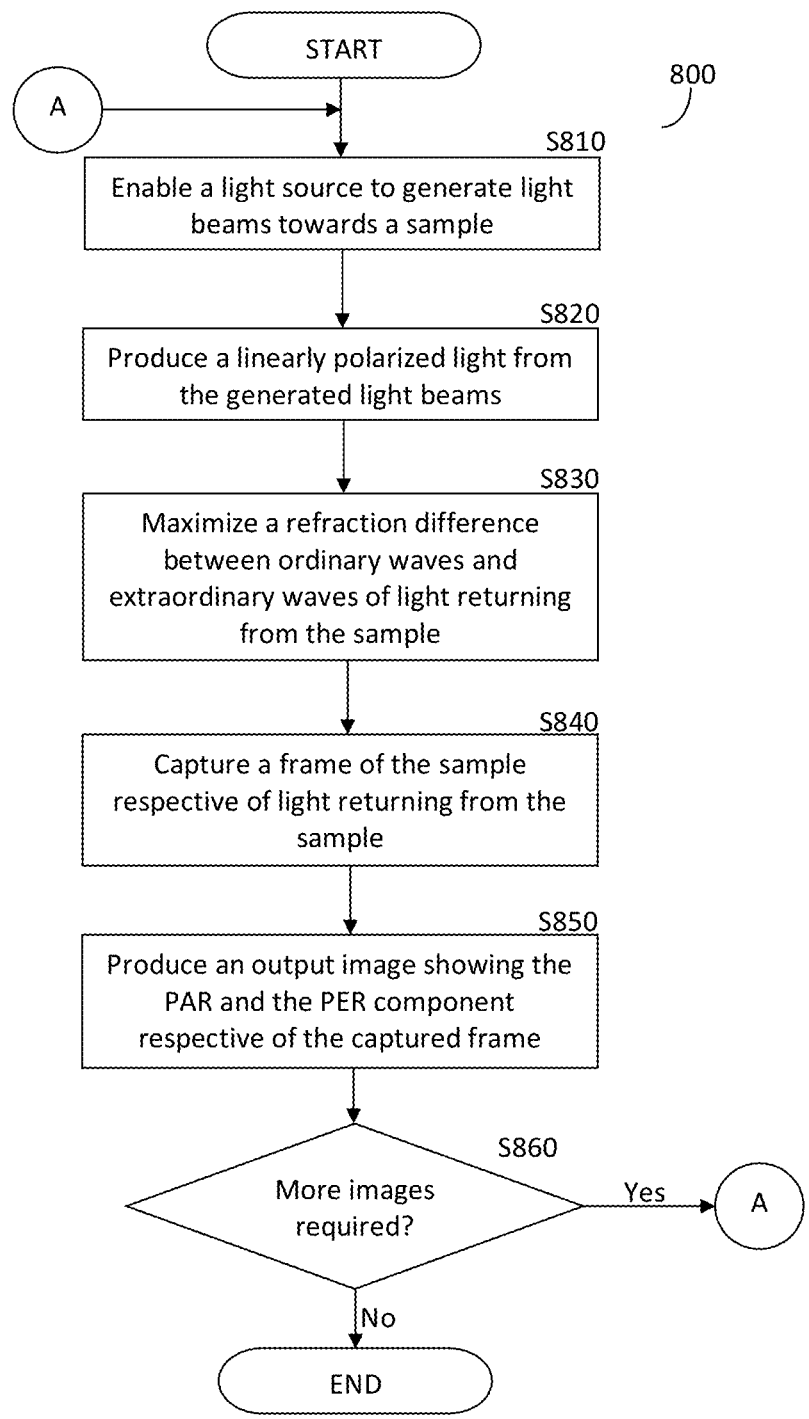
FIG. 8 is a flowchart describing a process of identifying the optical properties of a sample as a function of space according to an embodiment.

FIG. 8 depicts an exemplary and non-limiting flowchart 800 describing a process for identifying PAR and PER components as a function of space according to an embodiment. The method may be performed by the apparatus 300 discussed further herein above with respect to FIG. 3.

In S810, a generation of light beams by a light source (e.g., light source 120) is enabled. Such light beams are guided by an illumination optic (e.g., illumination optic 122) towards a sample such as sample 110.

In S820, the light beams with a specific polarization passes through a linear polarizer (e.g., linear polarizer 124) before they reach the sample to produce a linearly polarized light. It should be understood that the linear polarizer is configured to block waves of unwanted polarizations. In S830, the reflection difference between ordinary waves and extraordinary waves of light returning from the sample are maximized by a non-TIR BPP (e.g., non-TIR BPP 330).

According to an embodiment, the amount of waves returning from the sample 110 towards the non-TIR BPP is regulated by one or more aperture stops (e.g., aperture stops 340-1 and/or 340-2).

In S840, a frame of the sample is captured by a SE (e.g., SE 310) respective of the light returning from the sample. Such light contains the PAR and the PER components and it should be emphasized that the PAR and the PER components may be captured simultaneously by one SE. According to an embodiment, the light returning from the sample is guided by a detection optic unit (e.g., detection optic unit 320) towards the SE.

In S850, an output image is produced respective of the captured frame by employing at least one image processing technique on the frame using, for example, a processing unit (e.g., processing unit 352). As a non-limiting example, the diffuse component is separated from the specular reflection and the single-scattered (SS) components to show the difference between the PAR component and PER component in the output image (e.g., FIG. 7). According to an embodiment, the output image is displayed on a display. According to another embodiment, the captured frame, the polarization condition in which the frame was captured, and the output image are stored in a data storage unit (e.g., data storage 358). In S860, it is checked whether additional output images are required, and if so execution continues with S810; otherwise, execution terminates.

Figure 9:
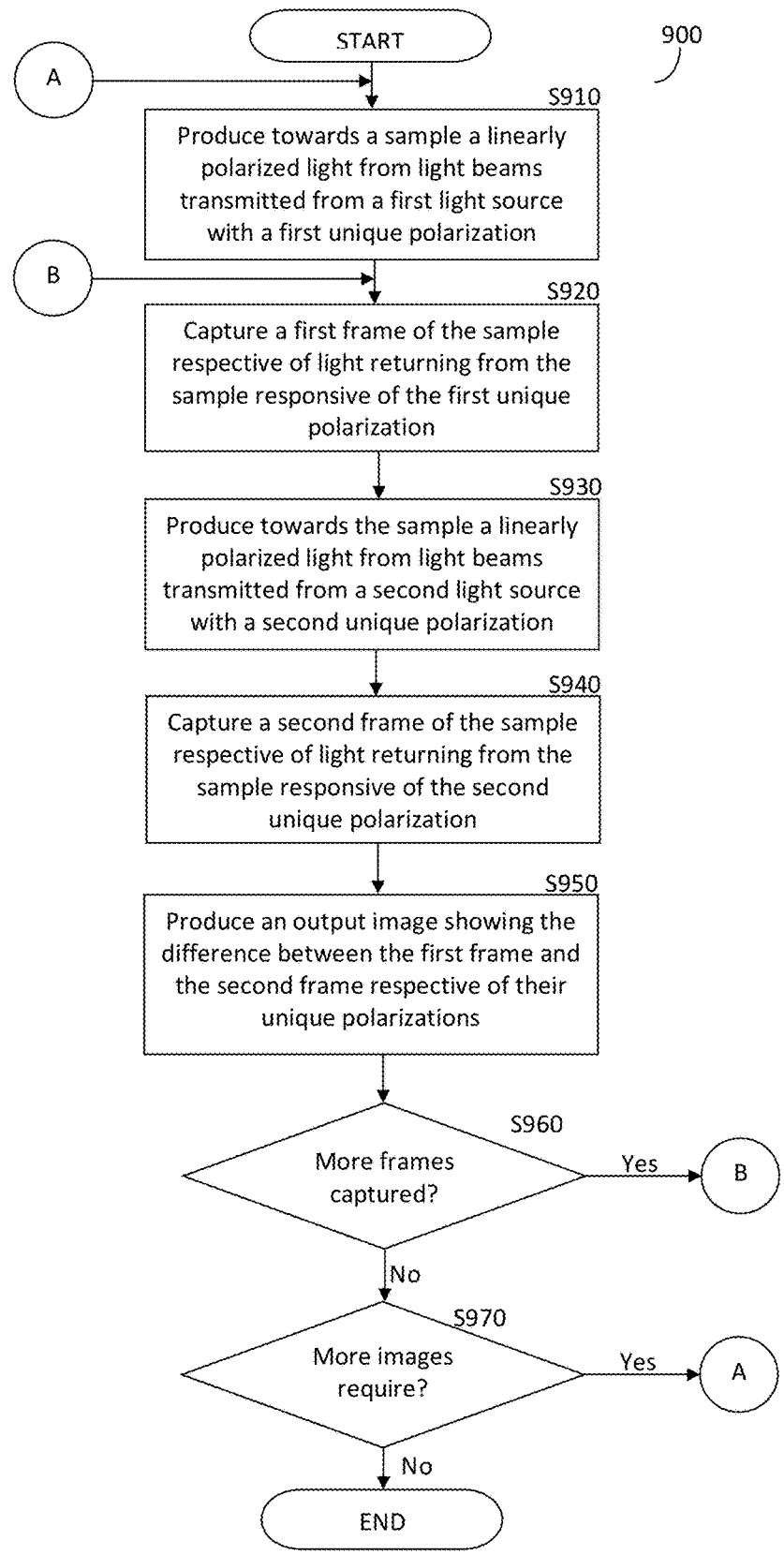
FIG. 9 is a flowchart describing a process of identifying the optical properties of a sample as a function of time according to an embodiment.

FIG. 9 shows an exemplary and non-limiting flowchart 900 describing a process of identifying the optical properties of a sample as a function of time according to an embodiment. Such process may be performed by the apparatus 400 discussed further herein above with respect to FIG. 4.

In S910, light beams are generated with a first unique polarization by a first light source (e.g., the light source 410-1). Such light beams may travel through a first linear polarizer (e.g., linear polarizer 414-1) before they reach a sample (e.g., the sample 110) to produce a first linearly polarized light. It should be noted that the first linear polarizer is used to block waves with unwanted polarizations. It should also be noted that the light beams are guided by an illumination optic (e.g., the illumination optic 412-1) towards the sample.

In S920, a first frame of the sample is captured by a SE (e.g., the SE 310) respective of the light returning from the sample and responsive of the first unique polarization. According to an embodiment, the light returning from the sample is polarized by a linear polarizer (e.g., the linear polarizer 414-3) and guided towards the SE by a detection optic unit (e.g., the detection optic unit 440). According to another embodiment, the first frame is stored in a data storage unit (e.g., data storage unit 358).

In S930, light beams are generated with a second unique polarization by a second light source (e.g., the light source 410-2). Such light beams may travel through a second linear polarizer (e.g., linear polarizer 414-2) before they reach the sample to produce a second linearly polarized light. It should be noted that the second linear polarizer is used to block waves with unwanted polarizations. It also should be noted that the light beams are guided by an illumination optic (e.g., the illumination optic 412-2) towards the sample.

In S940, a second frame of the sample is captured by the SE respective of the light returning from the sample and responsive of the second unique polarization. According to an embodiment, the light returning from the sample is polarized by the linear polarizer and guided towards the SE by the detection optic unit. According to another embodiment, the second frame is stored in the data storage unit.

In S950, an output image is produced by employing at least one image processing technique on at least the first and second frames using, for example, a processing unit (e.g., processing unit 352). As a non-limiting example, the first frame is compared to the second frame to show the difference between the PAR and PER component. It should be understood that while the first frame is captured respective of the PAR component, the second frame may be captured respective of the PER component, and vice versa. Thus, the first unique polarization represented in the first frame is compared to the second unique polarization represented in the second frame. Therefore, the image may be configured to show the difference between the various polarizations. According to an embodiment, the first frame and the second frame are retrieved from the data storage unit. According to another embodiment, the image is stored in the data storage unit, and/or is displayed on a display.

In S960, it is checked whether additional frames have been captured and, if so, execution continues with S920; otherwise, execution S970. In S970, it is checked whether additional polarization images are required to be produced and, if so, execution continues with S910; otherwise, execution terminates.

The certain embodiments disclosed herein can be implemented as hardware, firmware, software, or any combination thereof. Moreover, the software is preferably implemented as an application program tangibly embodied on a program storage unit or computer readable medium. The application program may be uploaded to, and executed by, a machine comprising any suitable architecture. Preferably, the machine is implemented on a computer platform having hardware such as one or more central processing units ("CPUs"), a memory, and input/output interfaces. The computer platform may also include an operating system and microinstruction code. The various processes and functions described herein may be either part of the microinstruction code or part of the application program, or any combination thereof, which may be executed by a CPU, whether or not such computer or processor is explicitly shown. In addition, various other peripheral units may be connected to the computer platform such as an additional data storage unit and a printing unit.

All examples and conditional language recited herein are intended for pedagogical purposes to aid the reader in understanding the disclosed embodiments and the concepts contributed by the inventor to furthering the art, and are to be construed as being without limitation to such specifically recited examples and conditions. Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future, i.e., any elements developed that perform the same function, regardless of structure. Furthermore, a non-transitory computer readable medium is any computer readable medium except for a transitory propagating signal.

What is claimed is:

1. A polarized light imaging apparatus for separating light from a superficial single-scattering layer of a sample and its deeper diffuse layer as a function of time, comprising:
   a controller;
   a first light source for producing light beams with a first polarization feature under the control of the controller;
   a second light source for producing light beams with a second polarization feature under the control of the controller;
   a first illumination optic coupled to the first light source, wherein the first illumination optic guides the light beams produced by the first light source towards the sample;
   a second illumination optic coupled to the second light source, wherein the second illumination optic guides the light beams produced by the second light source towards the sample;
   a first linear polarizer coupled to the first illumination optic, wherein the first linear polarizer is configured to produce a first linearly polarized light toward the sample respective of the light beams with the first polarization feature;
   a second linear polarizer coupled to the second illumination optic, wherein the second linear polarizer is configured to produce a second linearly polarized light toward the sample respective of the light beams with the second polarization feature;
   a third linear polarizer coupled to a detection optic unit, wherein the third linear polarizer is configured to produce a third linearly polarized light toward the detection optic unit; and
   a single polarization sensitive sensor element (SE) for capturing a plurality of frames of the sample respective of the detection optic unit,
   wherein each of the plurality of frames is captured respective of the first polarization feature and the second polarization feature, and
   wherein a polarization state of the first polarization feature is different from a polarization state of the second polarization feature.

2. The apparatus of claim 1, wherein the first polarization feature and the second polarization feature are produced respective of a predetermined time interval.

3. The apparatus of claim 1, wherein the detection optic unit is coupled to the SE and is configured to guide the linearly polarized light returning from the sample towards the SE.

4. The apparatus of claim 1, wherein each of the first light source and the second light source is equipped with a polarization separating mechanism to produce beams with a plurality of respective unique polarizations.

5. The apparatus of claim 1, wherein each of the first light source and the second light source is any one of: a LED, a polarizer, and a plastic light pipe.

6. The apparatus of claim 1, further comprising at least one light pipe configured to guide the light beams towards the sample.

7. The apparatus of claim 1, wherein the controller is further configured to process the plurality of frames captured by a processing unit to produce an output image representing the various polarizations.

8. The apparatus of claim 7, wherein the apparatus is further configured to perform at least one of: send the output image for storage in a data storage unit, and display the output image on a display.

9. The apparatus of claim 1, wherein the first and second illumination source are configured to produce respectively alternating square waves of light that proceed toward the sample, thereby the captured plurality of frames is respective of the first polarization feature and the second polarization feature.

10. A method for separating light from a superficial single-scattering layer of a sample and its deeper diffuse layer as a function of time, comprising:

enabling a first light source to generate a first light beam with a first polarization feature, wherein the first light beam is guided by a first illumination optic towards the sample, and wherein the first polarization feature is produced by a first linear polarizer;

enabling a second light source to generate a second light beam with a second polarization feature, wherein the second light beam is guided by a second illumination optic towards the sample, and wherein the second polarization feature is produced by a second linear polarizer;

capturing by a single polarization-sensitive sensor element (SE) a first frame of the sample respective of light returning from the sample responsive of the first light beam, wherein the returning light is proceeded by a third linear polarizer and adjusted by a detection optic;

capturing by the polarization-sensitive sensor element (SE), a second frame of the sample respective of the light returning from the sample responsive of the second light beam, wherein the returning light is proceeded by the third linear polarizer and adjusted by the detection optic; and calculating, using the first frame and the second frame, an output image representing the differences between the first light beam and the second light beam;

wherein a polarization state of the first polarization feature is different from a polarization state of the second polarization feature.

11. The method of claim 10, wherein the first polarization feature and the second polarization feature are produced respective of a predetermined time interval.

* * * * *